(12) United States Patent
Ontumi et al.

(10) Patent No.: US 9,161,891 B2
(45) Date of Patent: Oct. 20, 2015

(54) GELATIN ENCAPSULATED ORAL CARE COMPOSITION CONTAINING DENTAL OCCLUSION ACTIVES, HYDROPHOBIC VISCOSITY MODIFIER AND OIL CARRIER

(75) Inventors: Dennis Kembero Ontumi, Easton, PA (US); Sarita Vera Mello, North Brunswick, NJ (US); Suman Kumar Chopra, Monroe, NJ (US); James Richard Brown, Edison, NJ (US); Thomas James Boyd, Metuchen, NJ (US); Rahul Patel, Parsippany, NJ (US)

(73) Assignee: Colgate-Palmolive Company, New York, NY (US)

(*) Notice: Subject to any disclaimer, the term of this patent is extended or adjusted under 35 U.S.C. 154(b) by 177 days.

(21) Appl. No.: 13/995,512

(22) PCT Filed: Dec. 20, 2010

(86) PCT No.: PCT/US2010/061305
§ 371 (c)(1),
(2), (4) Date: Jun. 19, 2013

(87) PCT Pub. No.: WO2012/087279
PCT Pub. Date: Jun. 28, 2012

(65) Prior Publication Data
US 2013/0269132 A1    Oct. 17, 2013

(51) Int. Cl.
| | |
|---|---|
| *A61K 8/11* | (2006.01) |
| *A46B 11/00* | (2006.01) |
| *A61Q 11/00* | (2006.01) |
| *A61K 8/31* | (2006.01) |
| *A61K 8/44* | (2006.01) |
| *A61K 8/65* | (2006.01) |
| *A61K 8/81* | (2006.01) |
| *A61K 8/92* | (2006.01) |

(52) U.S. Cl.
CPC ............... *A61K 8/11* (2013.01); *A46B 11/001* (2013.01); *A61K 8/31* (2013.01); *A61K 8/44* (2013.01); *A61K 8/65* (2013.01); *A61K 8/8111* (2013.01); *A61K 8/8164* (2013.01); *A61K 8/922* (2013.01); *A61Q 11/00* (2013.01); *A61K 2800/31* (2013.01)

(58) Field of Classification Search
USPC ............ 424/10.4, 401; 222/541.6; 428/402.2; 427/2.18
See application file for complete search history.

(56) References Cited

U.S. PATENT DOCUMENTS

| | | | |
|---|---|---|---|
| 2,628,187 A * | 2/1953 | Frohmader et al. ............ 514/789 |
| 4,010,254 A | 3/1977 | Koulbanis et al. |
| 4,292,304 A * | 9/1981 | Barels et al. .................. 424/401 |
| 4,422,985 A | 12/1983 | Morishita et al. |
| 4,426,337 A | 1/1984 | Suzuki et al. |
| 5,028,432 A | 7/1991 | Chopra et al. |
| 5,037,698 A | 8/1991 | Brunel |
| 5,390,984 A | 2/1995 | Boucherie et al. |
| 5,393,796 A | 2/1995 | Halberstadt et al. |
| 5,478,570 A | 12/1995 | Sunohara et al. |
| 5,533,791 A | 7/1996 | Boucherie |
| 5,609,890 A | 3/1997 | Boucherie |
| 5,944,528 A | 8/1999 | Montgomery |
| 6,306,435 B1 | 10/2001 | Chen et al. |
| 6,514,558 B2 | 2/2003 | Cardinaels |
| 6,524,558 B2 | 2/2003 | Kleinberg et al. |
| 6,905,673 B2 | 6/2005 | Rajaiah et al. |
| 7,478,959 B2 | 1/2009 | Hohlbein |
| 7,601,002 B2 | 10/2009 | Milanovich et al. |
| 2002/0176827 A1 | 11/2002 | Rajaiah et al. |
| 2004/0237226 A1 | 12/2004 | Hohlbein et al. |
| 2004/0258630 A1 | 12/2004 | Boyd et al. |
| 2006/0045854 A1 | 3/2006 | Zaidel et al. |
| 2006/0083727 A1 | 4/2006 | Kajander et al. |
| 2006/0113333 A1 * | 6/2006 | Withers et al. ............. 222/541.6 |
| 2006/0134020 A1 | 6/2006 | Robinson et al. |
| 2007/0122359 A1 | 5/2007 | Wang et al. |
| 2009/0202450 A1 | 8/2009 | Prencipe et al. |
| 2009/0202456 A1 | 8/2009 | Prencipe et al. |
| 2009/0311200 A1 | 12/2009 | Lambert et al. |
| 2009/0320226 A1 | 12/2009 | Robinson et al. |
| 2010/0135921 A1 * | 6/2010 | Hughes et al. .................. 424/49 |
| 2010/0135932 A1 | 6/2010 | Deckner et al. |

FOREIGN PATENT DOCUMENTS

| | | |
|---|---|---|
| CA | 1182354 | 2/1985 |
| EP | 131235 | 5/2003 |

(Continued)

OTHER PUBLICATIONS

Biokyowa, Inc., 2007, "L-Arginine Material Safety Data Sheet," pp. 1-5.

(Continued)

*Primary Examiner* — Walter Webb

(57) ABSTRACT

A oral care composition includes: (a) a guanidine active; (b) a film-forming polymer; (c) a hydrophobic viscosity modifier in an amount sufficient to provide the oral care composition with a particle settling time greater than 20 minutes; and (d) an oil carrier. The guanidine active is preferably L-arginine. The film-forming polymer is preferably GANTREZ. The hydrophobic viscosity modifier is preferably a gelled mineral oil. The oil carrier is preferably a vegetable oil. A method of cleaning teeth includes applying to the teeth the oral care composition such that the oral care composition cleans the teeth. A oral care implement includes: a handle; a head mounted to the handle, the head having an outer surface and a plurality of tooth cleaning elements extending outwardly from the outer surface; and a gelatin capsule containing the oral care composition positioned on the head.

13 Claims, No Drawings

(56) References Cited

FOREIGN PATENT DOCUMENTS

| JP | S59-86132 | 6/1984 |
|---|---|---|
| JP | 2004-189749 | 7/2004 |
| WO | WO 99/06031 | 2/1999 |
| WO | WO 99/62471 | 12/1999 |
| WO | WO 2005/058267 | 6/2005 |
| WO | WO 2006/002806 | 1/2006 |
| WO | WO 2007/144189 | 12/2007 |
| WO | WO 2009/100277 | 8/2009 |
| WO | WO 2009/149030 | 12/2009 |
| WO | WO 2009/157956 | 12/2009 |
| WO | WO 2010/115041 | 10/2010 |
| WO | WO 2011/162756 | 12/2011 |

OTHER PUBLICATIONS

Biokyowa, Inc., 2010, "L-Arginine Free Base Certificate of Analysis".

Chemical Abstracts, "L-Arginine," Technical Information, CAS No. 74-79-3, retrieved from internet 2010.

International Search Report and Written Opinion in International Application No. PCT/US10/061305, mailed Oct. 27, 2011.

International Specialty Products, 1999, "Gantrez Copolymers Technical Profile" pp. 1-15.

ISP Chemicals Llc., 2009, "Gantrez® S-97 BF Material Safety Data Sheet," pp. 1-5.

ISP Technologies, Inc., 2010, "Gantrez S-97 BF Certificate of Analysis," pp. 1-2.

Ofner et al., 1987, "Swelling Studies of Gelatin II: Effect of Additives," J. Pharm. Sci. 76(9):715-723.

Pharmaceutical Resources, 1989, "Plastigel™ 5 Plasticized Hydrocarbon Gel Product Data Sheet," pp. 1-10.

Pharmaceutical Resources, Llc, 2009, "Plastigel-5 Certificate of Analysis".

Schiff et al., "Efficacy of a Dentifrice Containing Potassium Nitrate, Soluble Pyrophosphate, PVM/MA Copolymer, and Sodium Fluoride on Dentinal Hypersensitivity: A Twelve-Week Clinical Study," J. Clinical Dentistry 5:87-92.

Thau et al., 1965, "A New Procedure for the Preparation of Polyethylene-Mineral Oil Gels," J. Soc. Cosmetic Chemists 16:359-363.

Written Opinion in International Application No. PCT/US2010/061305, mailed Dec. 17, 2012.

\* cited by examiner

GELATIN ENCAPSULATED ORAL CARE COMPOSITION CONTAINING DENTAL OCCLUSION ACTIVES, HYDROPHOBIC VISCOSITY MODIFIER AND OIL CARRIER

FIELD OF THE INVENTION

The invention relates to encapsulated oral care compositions and oral care devices including same.

BACKGROUND

PCT/US2010/039677 discloses the use of arginine and a film-forming polymer of methylvinylether/maleic anhydride (GANTREZ S™) in a mouthwash to form a highly adherent film, which is effective to occlude dentinal tubules, and thereby reduce tooth sensitivity.

Other publications disclosing the use of arginine and GANTREZ in a oral care composition include US 20090202456 A1, US 20090311200 A1 and US 20100135932 A1.

Despite the foregoing developments, it is desired to provide dentinal tubule occlusion agents in gelatin encapsulated liquid oral care compositions. It is further desired to provide oral care devices comprising gelatin capsules containing dentinal tubule occlusion agents.

BRIEF SUMMARY

Various embodiments described herein satisfy the aforementioned needs, by providing gelatin encapsulated liquid oral care compositions containing dentinal tubule occlusion agents and oral care devices comprising same.

According to one aspect of the invention, a oral care composition comprises: (a) a guanidine active; (b) a film-forming polymer; (c) a hydrophobic viscosity modifier in an amount sufficient to provide the oral care composition with a particle settling time greater than 20 minutes; and (d) an oil carrier.

In certain embodiments, the oral care composition is encapsulated within a capsule comprising gelatin.

In certain embodiments, the guanidine active is provided in an amount effective to reduce dentinal hypersensitivity.

In certain embodiments, the guanidine active constitutes 1-10 wt. % of the oral care composition.

In certain embodiments, the guanidine active is L-arginine.

In certain embodiments, the film-forming polymer constitutes 1-5 wt. % of the oral care composition.

In certain embodiments, the film-forming polymer is a copolymer of methyl vinyl ether and maleic anhydride.

In certain embodiments, the hydrophobic viscosity modifier constitutes more than 4 wt. % of the oral care composition.

In certain embodiments, the hydrophobic viscosity modifier comprises a gelled mineral oil. In certain of these embodiments, the gelled mineral oil is a plastigel comprising polyethylene and mineral oil.

In certain embodiments, the oil carrier constitutes 60-80 wt. % of the oral care composition.

In certain embodiments, the oil carrier comprises at least one of a vegetable oil and silicone oil.

In certain embodiments, the oil carrier comprises a C6 to C12 triglyceride.

In certain embodiments, the oral care composition further comprises 5-25 wt. % of a flavoring agent and 0.1-5 wt. % of a sweetening agent.

In certain embodiments, the oral care composition further comprises at least one member selected from the group consisting of an abrasive, an anti-bacterial agent, a foaming agent, a whitening agent, an anti-calculus agent, a tartar control agent, an anti-inflammatory agent, an anticaries agent, a flavoring agent, a sweetening agent and a colorant.

In certain embodiments, the guanidine active is L-arginine, the hydrophobic viscosity modifier is a gelled mineral oil, the film-forming polymer is a copolymer of methyl vinyl ether and maleic anhydride, and the oil carrier is caprylic/capric triglyceride, and the oral care composition further comprises hydrated silica, sorbitol, sucralose, glycerin, a colorant and a flavoring agent.

In certain embodiments, the oral care composition has a viscosity from 300 to 800 cps.

According to another aspect of the invention, a method of cleaning teeth comprises applying to the teeth the oral care composition of the invention such that the oral care composition cleans the teeth.

According to still another aspect of the invention, a oral care implement comprises: a handle; a head mounted to the handle, the head comprising an outer surface and a plurality of tooth cleaning elements extending outwardly from the outer surface; and a gelatin capsule containing the oral care composition of the invention positioned on the head.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, terms "treatment" or "treating" are intended to include prophylaxis. The terms include amelioration, prevention and relief from the symptoms and/or effects associated with dentinal hypersensitivity. The terms "preventing" or "prevention" refer to administering the composition beforehand to forestall or obtund dentinal hypersensitivity. Persons of ordinary skill in the art of compositions for the treatment of dentinal hypersensitivity (to which the present method claims are directed) recognize that the term "prevent" is not an absolute term. Rather, the term is understood to refer to the prophylactic administration of a composition to diminish the likelihood or seriousness of a condition, and this is the sense intended.

An "orally acceptable amount" of a compound is an amount that is not harmful to a mammal when a composition containing such amount is retained in the mouth, without swallowing, for a period sufficient to permit application to an oral surface as provided herein. In general, such amount of the compound is not harmful even if the composition is unintentionally swallowed. An "orally acceptable carrier" denotes any vehicle or carrier that is not harmful to a mammal when such carrier is used in a composition that is retained in the mouth, without swallowing.

Formulated oral care compositions such as tooth pastes and gels contain a number of functional and active ingredients, each of which contribute to at least one desirable property. Properly formulated oral care compositions are suitable for regular use to promote oral health. Functional additives include foaming agents that disperse other ingredients and provide for delivery of the active and functional materials to the oral surfaces, and tartar control agents to prevent the formation of calculus on tooth surfaces, as well as aesthetic functional ingredients such as flavors and pigments. Active ingredients include anticaries agents that provide a source of fluoride ion upon use. Various compositions also contain compounds or components with antibacterial properties, for example to reduce the formation of plaque on the surfaces. Further active ingredients include those with anti-inflammatory properties for prophylaxis and treatment of conditions such as gingivitis.

Throughout this description, the expression "oral care active" denotes a component that provides an active effect during an oral care treatment. Oral care actives include, but are not limited to foaming agents, antibacterial agents, whitening agents, anti-calculus agents, antimicrobial agents, tartar control agents, anti-inflammatory agents, and the like.

The invention was motivated in part by a desire to provide a non-aqueous liquid oral care composition containing actives effective to treat or prevent dentinal hypersensitivity. Although arginine and GANTREZ were known to be useful for treating or preventing dentinal hypersensitivity when dissolved in a oral care composition, it was unexpected that arginine and GANTREZ suspended (undissolved) in an oil carrier would provide highly effective tubule occlusion.

It was also unexpected that hydrophilic actives, such as arginine and GANTREZ, incorporated into a vegetable oil center core of a gelatin capsule would create cosmetic instability as well as delivery issues. Without wishing to be bound by any theory, it is believed that the issues are caused by rapid migration of the hydrophilic active into the gelatin capsule during the cooling stage of manufacturing, when all layers of the capsule are effectively liquid. This migration causes "fish eye" defects in the capsule, presumably due to the compromised gelatin structure. In addition, the amount of hydrophilic active delivered is hampered since at least some of it (perhaps about 90%) is permanently bound to the gelatin capsule and not released or dissolved during brushing.

The invention is based in part on the discovery that deactivation of a hydrophilic active in a gelatin encapsulated oral care composition, and destabilization of the gelatin capsule can be prevented, reduced or delayed by suspending the hydrophilic active in an oil carrier containing a hydrophobic viscosity modifier, and subsequently incorporating the resulting oil carrier and suspended hydrophilic active into the gelatin capsule.

The hydrophobic viscosity modifier of the inventive oral care composition is, as the name implies, a hydrophobic ingredient, which increases the viscosity of the hydrophobic liquid. Gelled mineral oils are presently the most preferred examples of suitable hydrophobic viscosity modifiers. The gelled mineral oil is preferably a blend of mineral oil and polyethylene, and most preferably PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gels," J. Soc. Cosmetic Chemists, 16, 359-363 (1965). Suitable hydrophobic viscosity modifiers additional to gelled mineral oils, such as plastigels, can be identified by using the present disclosure as a guide.

In addition to the hydrophobic viscosity modifier, the oral care composition contains an oil carrier, such as vegetable oil and/or silicone oil. The oil carrier preferably constitutes 50-90 wt. %, more preferably 60-80 wt. %, and most preferably about 75 wt. % of the composition. Medium chain triglycerides (MCTs) are preferred as the oil carrier. MCTs are typically about 6 to about 12 carbons in length. MCTs can be vegetable oils. Caprylic/capric triglyceride is a non-limiting example of an MCT preferred for use in the invention.

The hydrophilic active preferably constitutes 0.0001-20 wt. % or 0.1-15 wt. % or 1-10 wt. % of the oral care composition. The hydrophilic active is preferably a guanidine active and/or a film-forming polymer.

The guanidine active is a compound containing a guanidine group capable of forming a guanidinium ion under conditions present in the oral cavity. Suitable guanidine actives include but are not limited to arginine bicarbonate, arginine hydroxide, arginine carbonate, arginine phosphate, arginine organic phosphate, arginine phytate, aminoguanidine and aminoguanidinium analogues. L-arginine is particularly preferred.

The guanidine active is provided in an amount effective to reduce dentinal hypersensitivity, and preferably constitutes 0.1-15 wt. % or 1-10 wt. % or 3-7 wt. % of the oral care composition.

The film-forming polymer is preferably a synthetic anionic polycarboxylate. Anionic polycarboxylates are generally employed in the form of their free acids or preferably partially or more preferably fully neutralized water soluble alkali metal (e.g., potassium and preferably sodium) or ammonium salts. Preferred film-forming polymers are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000.

One particularly preferred film-forming polymer is a synthetic copolymer comprises poly(methylvinylether/maleic acid). In another embodiment, a copolymer comprises poly (methyylvinylether/maleic acid) half esters. In another embodiment, a copolymer comprises poly(methylvinylether/ maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average). In a preferred embodiment, the copolymer has a molecular weight of 130,000. In an embodiment, a polymer has a molecular weight of 200,000. In an embodiment, a copolymer has a molecular weight of 690,000. In an embodiment, a copolymer has a molecular weight of 1,000,000. In an embodiment, a copolymer has a molecular weight of 1,250,000. In an embodiment, a copolymer has a molecular weight of 1,980,000. In another embodiment, a copolymer has a molecular weight of 2,500,000. In yet another embodiment, a copolymer has a molecular weight of 5,000,000.

Examples of these copolymers are available from ISP Corporation under the tradename GANTREZ, GANTREZ AN 139 (M.W. 1,100,000), GANTREZ AN 119 (M.W. 200,000); GANTREZ S-97 Pharmaceutical Grade (M.W. 1,500,000); GANTREZ AN 169 (M.W. 2,000,000), and GANTREZ AN 179 (M.W. 2,400,000); wherein the preferred copolymer is GANTREZ S-97 Pharmaceutical Grade (M.W. 1,500,000).

The film-forming polymer is provided in an amount effective to reduce dentinal hypersensitivity, and preferably constitutes 0.1-10 wt. % or 1-5 wt. % of the oral care composition.

In addition to the hydrophilic active, the hydrophobic viscosity modifier and the oil carrier, the oral care compositions may further contain one or more orally acceptable abrasives, flavorants, colorants, sweeteners, processing aids, and optionally water.

In certain embodiments, the oral care composition comprises, consists essentially of, or consists of 1 to 10 wt. %, preferably 2.5 to 7 wt. %, and most preferably 5 wt. % high cleaning abrasive, such that the total amount of abrasive delivered per application is 2 mg to 8 mg, preferably 3 mg to 6 mg, and most preferably about 4 mg of abrasive. The high cleaning abrasive is present in an orally acceptable carrier. A small amount of small particle size abrasive provides an improved stain removal effect.

It is preferred that the abrasive be selected from high cleaning silica, tetrasodium pyrophosphate (TSPP), sodium tripolyphosphate (STPP), and mixtures thereof. The abrasives typically have a weight mean particle size in the range 2 to 18 μm with at least 90% by weight of particles having a size below 20 μm, a Radioactive Dentine Abrasion (RDA) determined on an aqueous slurry of the silica powder of 90 to 230, a Pellicle Cleaning Ratio (PCR), when incorporated in a dental composition at 10% by weight, greater than 80, the ratio of PCR to RDA being in the range 0.4:1 to less than 1:1 and having a Plastics Abrasion Value (PAV) in the range of 1 to 20.

The preferred abrasives are silicas having a particularly effective ability to clean, which is demonstrated by relatively high PCR values exhibited at conventional RDA values in oral care compositions containing a relatively small amount of the silica. Although the PCR to RDA ratio is less than 1, the RDA value preferably is higher than conventional silicas with a higher PCR to RDA ratio and, when compared to these products, a higher PCR is achievable with the same quantity of silica. Plastics Abrasion Values are a measure of the amount of scratching produced on a surface by the silica and are therefore indicative of possible damage to teeth. The silicas useful possess a moderate PAV but high PCR, which indicates good cleaning without excessive damage.

The amorphous silicas useful preferably have an oil absorption, using linseed oil, in the range 70 to 150 cm$^3$/100 g and, more preferably, the oil absorption is in the range 75 to 130 cm$^3$/100 g. Also, the amorphous silica preferably has a BET surface area in the range 10 to 450 m$^2$ g$^{-1}$, and, more preferably, the BET surface area is in the range 50 to 300 m$^2$ g$^{-1}$.

The weight mean particle size of the silica can be determined using a Malvern Mastersizer™ and a preferred material may have a weight mean particle size in the range 5 to 10 μm. The particle size distribution and, hence, the proportion of particles having a size below any particular value can be determined by the same technique. For the amorphous silica, at least 90% of the particles by weight preferably have a size below 17 μm.

In a particular embodiment, the weight mean particle size of the abrasives useful in the embodiments is in the range of 3 to 7 μm, with at least 90% of the particles by weight having a size below 16 μm, preferably below 12 μm.

In a particular embodiment, the silica is in the form of particles of a size such that they are effective to occlude dentinal tubules. Thus, the silica particles preferably have an average diameter of 0.5-10 microns or 1-9 microns or 2-7 microns, with an average diameter below 5 microns being most preferred.

The Radioactive Dentine Abrasion (RDA) of the silicas has a value in the range 100 to 220. More commonly, the RDA has a value in the range 120 to 200 and, frequently, the RDA is above 140. Generally, silicas having a PAV above 15 will have an RDA above 120 and those having a PAV above 17 have an RDA above 140.

The PCR (measured in a dental composition at 10% by weight) of the amorphous silica is greater than 85, preferably greater than 90 and more preferably greater than 95. The PCR:RDA ratio is preferably in the range 0.5:1 to 0.9:1.

The amorphous silica preferably has a pH value, measured on a 5% by weight suspension, in the range 5 to 8, more preferably in the range 6 to 7.5. The amount of water present on the amorphous silica suitable for use in a dental composition, as measured by the ignition loss at 1000° C., is usually up to 25% by weight and preferably up to 15% by weight. Usually the ignition loss at 1000° C. is more than 4% by weight.

Colorants such as pigments and dyes may be used in the composition. Pigments include nontoxic, water insoluble inorganic pigments such as titanium dioxide and chromium oxide greens, ultramarine blues and pinks and ferric oxides. The pigments have a particle size in the range of 5-1000 microns, preferably 250-500 microns, and are present at a concentration of 0.5 to 3% by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium), FD&C Blue No. 1 (disodium salt of dibenzyldiethyldiaminotriphenyl-carbinol trisulfonic acid of indigotin) and mixtures thereof in various proportions. Preferred dye concentrations range from 0.0005 to 1% of the total weight.

Any suitable flavoring or sweetening agent may also be incorporated in the oral care composition. Examples of suitable flavoring constituents include flavoring oils, as for example, oils of spearmint, peppermint, wintergreen, sassafras, clove, sage, eucalyptus, marjoram, cinnamon lemon, and orange, and methyl salicylate. Suitable sweetening agents include sucrose, sucralose, lactose, maltose, sorbitol, xylitol, sodium cyclamate, perillatine, and sodium saccharin. Suitably, flavoring materials are included in the oral care composition in an amount of 5% to 25% by weight, more preferably 10% to 20% by weight, and most preferably about 15% by weight. The sweetening agents may comprise 0.1 to 5% by weight, more preferably 0.25 to 2% by weight, and most preferably about 0.5% by weight of the oral care components.

The oral compositions optionally contain one or more other non-active ingredients. Non-limiting examples include diluents, bicarbonate salts, pH modifying agents, foam modulators, thickening agents, viscosity modifiers, pigmenting agents, sweetening agents, flavorants and colorants. Tooth pastes, tooth gels, and other oral care compositions are formulated with these and optionally other additives according to known principles.

The oral care composition is encapsulated in a gelatin capsule. Encapsulating liquid or aqueous compositions in a gelatin capsule can be accomplished using techniques known in the art and described in, for example, U.S. Pat. Nos. 4,422,985, 4,426,337 and 5,478,570. The process typically entails forming a jet of the oral care composition and a jet of the coating material (e.g., gelatin) coaxial with the jet of oral care composition, heating the coaxial jets (optionally with a third coaxial heating element or hot air) and introducing the components into a cooling liquid to form capsules formed of the oral care composition, coated with the gelatin. Although the oral care composition is preferably prepared in the absence of alcohol, any alcohol present in the oral care preferably is evaporated during the heating of the respective components. Preferably, the gelatin comprises from 6 to 15% of the total weight of the encapsulated oral care composition (i.e., the capsule and the oral care composition), more preferably 8 to 12%, and most preferably about 9%. Similarly, the oral care composition comprises 85 to 94% of the total weight of the encapsulated oral care composition, more preferably 88 to 92, and most preferably about 91%.

In one preferred aspect of the invention, the aforementioned encapsulated oral care composition is positioned on an oral care implement. For example, the encapsulated oral care composition can be positioned on the head of the oral care implement. This can be accomplished by positioning the encapsulated oral care composition within or between the cleaning elements of the oral care implement. When applied to such a tooth brushing device, the amount of oral care composition within the capsule typically ranges 45 mg to 80 mg, preferably 50 mg to 75 mg, and most preferably about 6.4 mg of oral care.

The oral care implement may include a rupturable dispenser containing the oral care composition, as a connected unit or the various other combinations of components and materials as described. A dispenser containing a oral care, such as the oral care composition described herein, or other oral care material can be connected in the bristle or cleaning element portion of the oral care implement for dispensing the oral care composition to the teeth. In one construction, the oral care elements are configured to slow a radial flow of the oral care composition released from the dispenser near an interior region of the carrier and increase a radial flow of the oral care material away from the interior region.

The composition has been described above with respect to several preferred embodiments. Further non-limiting description is provided in the Examples that follow.

EXAMPLES

Example 1

As noted above, the inventors believe that the beneficial effects provided by the invention are related in part to preventing or delaying migration of hydrophilic actives into the gelatin capsule during the cooling stage of manufacturing, when all layers of the capsule are effectively liquid. Thus, the particle settling times for a series of formulations were studied along with the viscosity of the formulations. The particle settling time for a given formulation should be predictive of the migration of hydrophilic actives from that formulation into a gelatin capsule. Viscosities were measured to identify any relationship between viscosity and particle settling time.

These values were compared with a reference sample, WISP™ PLUS WHITENING, which has a viscosity of 317 cps and has a particle settling time of 20 minutes. The reference sample viscosity of 317 cps is sufficiently low such that it can be processed without difficulty. However, the particle settling time is insufficient to avoid the aforementioned problems caused by the rapid migration of hydrophilic actives into a gelatin capsule. Particle settling time was determined by visually monitoring the migration of suspended powdered particles to the bottom of a vessel. A stop watch was utilized to record the time it took for the powder particles to completely settle to the bottom of the vessel.

Thus, test formulations were evaluated relative to the reference (control) formulation, The results are given in Table 1 below. Formulations with particle settling times longer than 20 minutes and with viscosities equal to or less than about 317 cps are ideal. These formulations will prevent the hydrophilic actives from substantially migrating into the gelatin capsule during the cooling/solidifying stage of the capsule production, but have a viscosity sufficiently low such that they are amenable to current processing conditions. Table 1 shows that several of the test formulations have viscosities within the preferred range below 800 cps. It is preferred that the viscosity be less than or equal to 327 cps or 300-800 cps or 150-330 cps.

TABLE 1

Viscosity and Settling Time for Control and Test Formulations

| Ingredient | Control | Formula 1 | Formula 2 | Formula 3 |
|---|---|---|---|---|
| Caprylic/capric triglyceride | 73.5 | 63.5 | 67.5 | 69.5 |
| L Arginine | x | 5 | 5 | 5 |
| Gantrez S -97 | x | 2 | 2 | 2 |
| Plastigel | x | 8 | 4 | 2 |
| Flavor | 15 | 15 | 15 | 15 |
| WS3 cooling | 1.5 | 1.5 | 1.5 | 1.5 |
| Sucralose + EtOH | 5 | 5 | 5 | 5 |
| AC 43 Silica | 5 | X | X | X |
| Total | 100 | 100 | 100 | 100 |
| Viscosity | 327 cps | 773 | 550 | 350 |
| Time | 20 mins | >60 min | 20 mins | 20 mins |

Example 2

In vitro efficacy was tested via hydraulic conductance method. Dentinal fluid flow is measured with a flow-meter (Flodec) attached to a Pashley's cell. A sample disk is tested before and after product application in order to provide its own baseline. Percentage of flow reduction is calculated as the difference in flow before and after treatment. A bead filled with the active formula prototype was place gently on the surface of the disk mounted on a Pashley cell, followed by hand brushing for one minute with a modified mini brush. Excess of product was rinsed with PBS and flow was recorded after 10 and 15 minutes under simulated pulpal pressure of 70 cm water. After 15 minutes, flow reduction on the sample was measured at 92.42%.

Repetition of the foregoing experiments utilizing a modified WISP brush showed that efficacy did not diminish. The mounted dentin disks were brushed for one minute with a WISP brush and the oral care composition. These brushing experiments supported the use of the brush as a means of delivery of product unto the tooth surface.

An embodiment of the inventive oral care composition was applied on dentin disks mounted on Pashley's cell for 5 min. Excess product was rinsed from the disks with PBS and flow was recorded after 15 minutes under simulated pulpal pressure of 70 cm $H_2O$. The inventive oral care composition showed a fluid flow reduction of about 90%. A control sample consisting of the encapsulated oral care composition of current WISP products showed a flow reduction of less than 25%.

The invention has been described above with respect to various preferred aspects; however it is to be understood the invention is not limited to the disclosed embodiments. Variations and modifications that will occur to the person of skill in the art are also part of the invention, which is defined in the appended claims.

What is claimed is:

1. A oral care composition comprising:
   (a) a guanidine active, wherein the active is L-arginine;
   (b) a film-forming polymer, wherein the polymer is a copolymer of methyl vinyl ether and maleic anhydride;
   (c) a hydrophobic viscosity modifier in an amount sufficient to provide the oral care composition with a particle settling time greater than 20 minutes; and
   (d) an oil carrier, wherein the oil carrier is caprylic/capric triglyceride wherein the oral care composition is encapsulated within a capsule comprising gelatin, and wherein the hydrophobic viscosity modifier comprises a gelled mineral oil and constitutes more than 4 wt. % of the oral care composition.

2. The oral care composition of claim 1, wherein the guanidine active constitutes 1-10 wt. % of the oral care composition.

3. The oral care composition of claim 1, wherein the film-forming polymer constitutes 1-5 wt. % of the oral care composition.

4. The oral care composition of claim 1, wherein the gelled mineral oil comprises a blend of polyethylene and mineral oil.

5. The oral care composition of claim 1, wherein the oil carrier constitutes 60-80 wt. % of the oral care composition.

6. The oral care composition of claim 1, wherein the oral care composition further comprises 5-25 wt. % of a flavoring agent and 0.1-5 wt. % of a sweetening agent.

7. The oral care composition of claim 1, wherein the oral care composition further comprises at least one member selected from the group consisting of an abrasive, an antibacterial agent, a foaming agent, a whitening agent, an anticalculus agent, a tartar control agent, an anti-inflammatory agent, an anticaries agent, a flavoring agent, a sweetening agent and a colorant.

8. The oral care composition of claim 1, wherein the composition further comprises hydrated silica, sorbitol, sucralose, glycerin, a colorant and a flavoring agent.

9. A method of cleaning teeth comprising applying to the teeth the oral care composition of claim 1 such that the oral care composition cleans the teeth.

10. An oral care implement comprising:
    a handle;
    a head mounted to the handle, the head comprising an outer surface and a plurality of tooth cleaning elements extending outwardly from the outer surface; and
    a gelatin capsule containing the oral care composition of claim 1 positioned on the head.

11. The oral care implement of claim 10, wherein the cleaning elements are constructed of an elastomeric material.

12. The oral care implement of claim 10, wherein the capsule is positioned within and surrounded by the cleaning elements.

13. The oral care composition of claim 2, wherein:
    the film-forming polymer constitutes 1-5 wt. % of the oral care composition;
    and
    the oil carrier constitutes 60-80 wt. % of the oral care composition.

* * * * *